US012705999B2

(12) United States Patent
Park et al.

(10) Patent No.: US 12,705,999 B2
(45) Date of Patent: Aug. 11, 2026

(54) METHOD FOR PROVIDING CUSTOMIZED ONLINE EDUCATION CONTENT FOR REHABILITATION FOR HEARING LOSS PATIENT

(71) Applicant: THE CATHOLIC UNIVERSITY OF KOREA INDUSTRY—ACADEMIC COOPERATION FOUNDATION, Seoul (KR)

(72) Inventors: Shi Nae Park, Seoul (KR); Jae Sang Han, Seoul (KR); Jae Hyuk Lee, Seongnam (KR); Young Ho Son, Seoul (KR)

(73) Assignee: THE CATHOLIC UNIVERSITY OF KOREA INDUSTRY-ACADEMIC COOPERATION, Seoul (KR)

( * ) Notice: Subject to any disclaimer, the term of this patent is extended or adjusted under 35 U.S.C. 154(b) by 0 days.

(21) Appl. No.: 18/716,879

(22) PCT Filed: Dec. 6, 2022

(86) PCT No.: PCT/KR2022/019734
§ 371 (c)(1),
(2) Date: Jun. 5, 2024

(87) PCT Pub. No.: WO2023/106802
PCT Pub. Date: Jun. 15, 2023

(65) Prior Publication Data

US 2025/0037600 A1 Jan. 30, 2025

(30) Foreign Application Priority Data

Dec. 6, 2021 (KR) ........................ 10-2021-0173210

(51) Int. Cl.
*G09B 7/08* (2006.01)
*G16H 10/20* (2018.01)
(Continued)

(52) U.S. Cl.
CPC ............... *G09B 7/08* (2013.01); *G16H 10/20* (2018.01); *G16H 50/20* (2018.01); *A61B 5/16* (2013.01);
(Continued)

(58) Field of Classification Search
CPC ........ G16H 50/20; G16H 10/20; G16H 40/67; A61F 11/00; A61B 5/4088; A61B 5/16;
(Continued)

(56) References Cited

U.S. PATENT DOCUMENTS 6,336,089 B1 * 1/2002 Everding ............... G09B 19/06 434/169
11,605,384 B1 * 3/2023 Dalton .................... G10L 15/08
(Continued)

FOREIGN PATENT DOCUMENTS

JP H06114038 A 4/1994
KR 20160126297 A 11/2016
(Continued)

OTHER PUBLICATIONS

International search report of PCT/KR2022/019734, Mar. 13, 2023, English translation.

*Primary Examiner* — Jack Yip
(74) *Attorney, Agent, or Firm* — STIP Law Group, LLC

(57) ABSTRACT

A method by which a chatbot application executed by at least one processor of a terminal provides a chatbot for rehabilitation education for a hearing loss patient, according to an embodiment of the present disclosure, includes: executing the chatbot that provides hearing loss rehabilitation content that is interactive learning content for hearing rehabilitation education for the hearing loss patient; determining the type of hearing loss rehabilitation content on the basis of the executed chatbot; providing the hearing loss rehabilitation content according to the determined type;
(Continued)

acquiring user response data regarding an audio quiz of the provided hearing loss rehabilitation content; performing a correct/wrong processing process for determining whether or not the acquired user response data is a correct answer, and providing a result of the performed correct/wrong processing process.

12 Claims, 8 Drawing Sheets

(51) Int. Cl.

| | |
|---|---|
| ***G16H 50/20*** | (2018.01) |
| *A61B 5/00* | (2006.01) |
| *A61B 5/16* | (2006.01) |
| *A61F 11/00* | (2022.01) |
| *G06F 3/16* | (2006.01) |
| *G09B 7/00* | (2006.01) |
| *G16H 40/67* | (2018.01) |
| *H04R 25/00* | (2006.01) |

(52) U.S. Cl.
CPC .......... *A61B 5/4088* (2013.01); *A61B 5/4803* (2013.01); *A61F 11/00* (2013.01); *G06F 3/16* (2013.01); *G09B 7/00* (2013.01); *G16H 40/67* (2018.01); *H04R 25/70* (2013.01)

(58) Field of Classification Search
CPC .......... A61B 5/4803; G09B 7/08; G09B 7/00; G06F 3/16; H04R 25/70
See application file for complete search history.

(56) References Cited

U.S. PATENT DOCUMENTS

2001/0036619 A1* 11/2001 Kerwin .................... G09B 7/02 434/118
2004/0064066 A1* 4/2004 John ........................ A61B 5/38 600/559
2005/0287501 A1* 12/2005 Sweetow ............... G09B 23/28 434/169
2006/0029912 A1* 2/2006 Kearby .................... G09B 5/04 434/116
2008/0254426 A1* 10/2008 Cohen ...................... G09B 5/06 434/308
2017/0046971 A1 2/2017 Moreno
2020/0074294 A1* 3/2020 Long ...................... G06N 3/044
2020/0118691 A1* 4/2020 Kiljanek ................ G06N 20/00
2020/0143701 A1* 5/2020 Letzt .................... A61B 5/4833
2021/0005305 A1* 1/2021 Lee ...................... A61B 5/4836
2021/0168544 A1* 6/2021 May ...................... G06F 16/683
2022/0165371 A1* 5/2022 Shriberg ................ G16H 10/60
2022/0201404 A1* 6/2022 Xu ......................... G16H 10/20
2022/0386902 A1* 12/2022 Vanpoucke ............ A61B 5/123

FOREIGN PATENT DOCUMENTS

KR 101984991 B1 6/2019
KR 20190086868 A 7/2019
KR 102179726 B1 11/2020
KR 20200129385 A 11/2020

* cited by examiner

METHOD FOR PROVIDING CUSTOMIZED ONLINE EDUCATION CONTENT FOR REHABILITATION FOR HEARING LOSS PATIENT

CROSS-REFERENCE TO RELATED APPLICATIONS

This application is the U.S. National Phase under 35 U.S.C. § 371 of International Application No. PCT/KR2022/019734, filed on Dec. 6, 2022, which in turn claims the benefit of Korean Application No. 10-2021-0173210, filed on Dec. 6, 2021, the disclosures of which are incorporated by reference into the present application.

TECHNICAL FIELD

The present disclosure relates to a method for providing a chatbot for rehabilitation education for a hearing loss patient and a system therefor, and more specifically, to a method and system for providing a chatbot for rehabilitation education for a hearing loss patient that provides interactive hearing rehabilitation education content to correct speech language cognitive processing of the hearing loss patient.

BACKGROUND ART

Hearing loss is a disease that occurs due to problems in a part of the auditory circuit, which consists of the auricle that receives sound, the eardrum or small bones (ossicles) of the middle ear, the cochlea, the auditory nerve, and the brain that analyzes the same in a complex manner. When the symptoms are mild, a hearing loss patient may not be able to hear small sounds, but in severe cases, the hearing loss patient may not be able to recognize external sounds.

Such hearing loss, which occurs due to various causes such as aging, causes serious issues in communication in daily life. For example, it is inevitable that a hearing loss patient will face difficult and embarrassing situations in most situations in daily life with family, acquaintances, and work, including interruptions in conversation.

In addition, when mild hearing loss is left untreated, there is a risk that the incidence of dementia may increase two-fold, and severe hearing loss may increase the incidence of dementia of up to five-fold. In 2017, hearing aids accounted for about 61% or 65 billion won out of 106.5 billion won in government grants for assistive devices for the disabled (National Health Insurance Service 2017), causing social losses.

However, according to an announcement by the Health Insurance Review and Assessment Service, the number of hearing loss patients is rapidly increasing from 277,000 in 2012 to 349,000 in 2017, showing an average annual increase of 4.8%. According to the results of the National Health and Nutrition Survey, among Koreans, the prevalence of bilateral hearing loss in people aged 12 or above was 4.5%, and in people aged 65 or above was 25.9%, showing that one or more in 4 elderly people have hearing loss.

In addition, in 2020, the number of people with hearing loss in Korea is estimated at about 8.09 million, of which about 1.85 million are over 65 years old, accounting for 25% of the total.

Accordingly, recently, the need for rehabilitation education for the increasing number of hearing loss patients has become important.

In general, hearing loss rehabilitation education focuses on the everyday speech and conversation cognition that subjects who have been fitted with hearing aids or are in the early or middle stages of hearing loss talk and listen to in their daily lives.

In other words, the purpose of the hearing loss rehabilitation education is to supplement and improve speech perceptivity due to hearing loss by improving perceptivity of conversations and sentences that go on in an individual's life pattern.

However, the development of a system with a training process optimized for such hearing loss rehabilitation education is insufficient, so the development and introduction of technology therefor is required.

DETAILED DESCRIPTION OF INVENTION

Technical Problems

The present disclosure has been devised to obviate the above limitation. An aspect of the present disclosure is directed to implementing a method and system for providing a chatbot for rehabilitation education for a hearing loss patient that provides interactive hearing rehabilitation education content to correct speech language cognitive processing of the hearing loss patient.

Technical aspects to be achieved by the present disclosure and embodiments according to the present disclosure are not limited to the technical aspects described above, and other technical aspects may also be addressed.

Technical Solution

A method by which a chatbot application executed by at least one processor of a terminal provides a chatbot for rehabilitation education for a hearing loss patient, according to an embodiment of the present disclosure, includes: executing the chatbot that provides hearing loss rehabilitation content that is interactive learning content for hearing rehabilitation education for the hearing loss patient; determining the type of hearing loss rehabilitation content on the basis of the executed chatbot; providing the hearing loss rehabilitation content according to the determined type; acquiring user response data regarding an audio quiz of the provided hearing loss rehabilitation content; performing a correct/wrong processing process for determining whether or not the acquired user response data is a correct answer; and providing a result of the performed correct/wrong processing process.

In this connection, the hearing loss rehabilitation content is question-and-answer type learning content that asks questions based on the audio quiz, which is a quiz based on predetermined speech data, and acquires the user response data for the audio quiz.

In addition, the determination of the type of hearing loss rehabilitation content includes selecting at least one problem type among a word-type problem type that provides the audio quiz in word units and a sentence-type problem type that provides the audio quiz in sentence units.

In addition, the provision of the hearing loss rehabilitation content according to the determined type includes outputting the audio quiz a predetermined number of times based on a single word or sentence, and the acquisition of the user response data includes acquiring single user response data.

In addition, the provision of the hearing loss rehabilitation content according to the determined type includes outputting the audio quiz a predetermined number of times based on a plurality of words or sentences, and the acquisition of the user response data includes a plurality of pieces of user response data.

In addition, the provision of the hearing loss rehabilitation content according to the determined type includes providing problem guidance text, an audio quiz start button, multiple choice selection items, and a timer interface.

In addition, the provision of the hearing loss rehabilitation content according to the determined type further includes providing wrong answer guidance text, a skip button, and a restart button when the user response data is processed as a wrong answer.

In addition, the acquisition of the user response data includes acquiring the user response data based on at least one input of an input of user choices to select at least one of a plurality of choices included in the multiple choice selection items of the hearing loss rehabilitation content or a user speech input based on a speech input user interface of the hearing loss rehabilitation content.

In addition, the acquisition of the user response data may further include, when the hearing loss rehabilitation content is the word-type problem type and the user speech input is a sentence-type speech input, converting the sentence-type speech input into a word-type speech input based on correct answer data of the audio quiz.

In addition, the performance of the correct/wrong processing process includes converting the user speech input into at least one piece of text data using a predetermined deep learning model, and determining the correct answer by comparing the at least one piece of text data with the correct answer data of the audio quiz.

In addition, the performance of the correct/wrong processing process may further include acquiring a matching rate between each of the at least one piece of text data and the correct answer data when all pieces of the at least one piece of text data is processed as a wrong answer, and providing a my-input selection item when at least one of the acquired at least one matching rate satisfies a predetermined standard value or more, wherein the my-input selection item includes an interface for selecting text corresponding to the user speech input based on at least one text choice.

In addition, the provision of the may-input selection item includes providing the text choice based on at least one of the at least one piece of text data, the correct answer data, or an additional text separately generated with a predetermined similarity to the text data and the correct answer data.

In addition, the method for providing a chatbot for rehabilitation education for a hearing loss patient according to an embodiment of the present disclosure further includes training the deep learning model based on at least one training data set among a first training data set based on text data matching the correct answer data among the user speech input and the at least one piece of text data, and a second training data set based on a text choice selected based on the user speech input and an interface of the my-input selection item.

A system for providing a chatbot for rehabilitation education for a hearing loss patient according to an embodiment of the present disclosure includes: at least one display that outputs hearing loss rehabilitation content; at least one memory; and at least one processor, wherein at least one application that is stored in the memory and executed by the processor to provide the chatbot for rehabilitation education for the hearing loss patient: executes the chatbot that provides the hearing loss rehabilitation content that is interactive learning content for hearing rehabilitation education for the hearing loss patient; determines the type of hearing loss rehabilitation content on the basis of the executed chatbot; provides the hearing loss rehabilitation content according to the determined type; acquires user response data regarding an audio quiz of the provided hearing loss rehabilitation content; performs a correct/wrong processing process for determining whether or not the acquired user response data is a correct answer; and provides a result of the performed correct/wrong processing process.

Effect of Invention

The method and system for providing a chatbot for rehabilitation education for a hearing loss patient according to an embodiment of the present disclosure implement the chatbot for rehabilitation education for the hearing loss patient that provides interactive hearing rehabilitation education content to correct speech language cognitive processing of the hearing loss patient, thereby providing an easy hearing loss rehabilitation education process anytime, anywhere in an interactive manner optimized for hearing loss rehabilitation education.

The effects of the present disclosure are not limited to those mentioned above, and other effects not mentioned may be clearly understood by those skilled in the art from the following description.

BEST MODE FOR CARRYING OUT THE INVENTION

Figure 1:
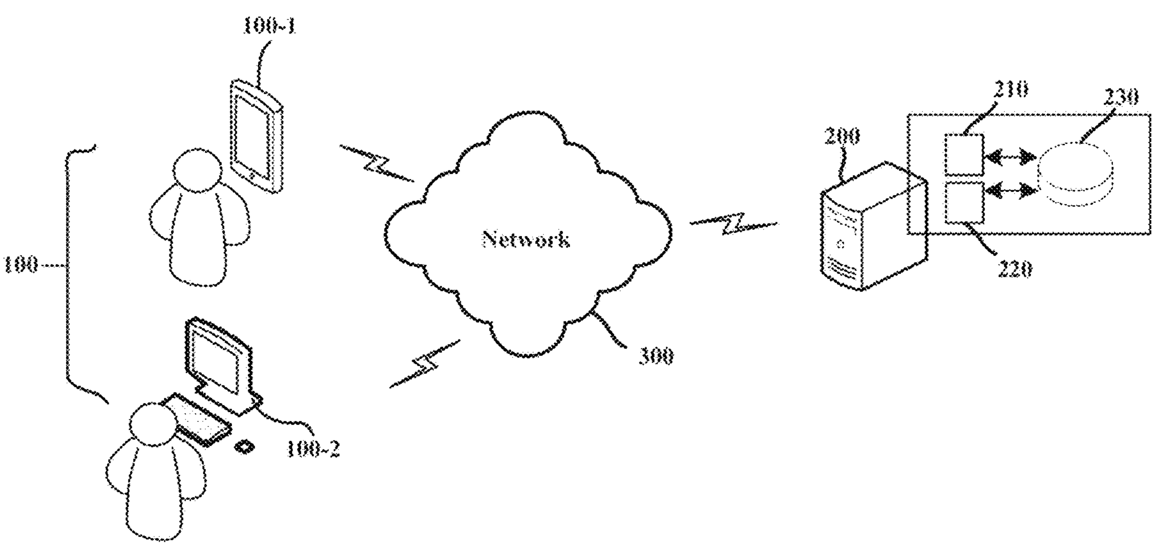
FIG. 1 is a conceptual diagram of a system for providing a chatbot for rehabilitation education for a hearing loss patient according to an embodiment of the present disclosure.

Embodiments of the present disclosure will be shown in the drawings and described in detail through a detailed description. However, the present disclosure may be variously modified and embodied in a variety of different embodiments. Advantages and features of the present disclosure and implementation methods thereof will be clarified through the following embodiments described with reference to the accompanying drawings. Therefore, the present disclosure is not limited to these embodiments introduced hereinafter and might be embodied in a different shape from these embodiments. The terms “first,” “second,” and so on in the present disclosure are used for distinguishing one component from the other components, but they do not specify limited meanings. Also, the singular forms used in the present disclosure are intended to include the plural forms, unless the context clearly indicates otherwise. Moreover, the terms “comprises” and/or “having” described in the present disclosure specify the presence of stated components and/or features, but do not preclude the presence or addition of one or more other components and/or features. Furthermore, the size or the thickness of each component in the drawings can be exaggerated or reduced for the definiteness of explanation. For example, the size and the thickness of each component in the drawings are arbitrarily represented for the convenience of explanation. In accordance therewith, the present disclosure is not limited to the matters shown in the drawings.

Reference will now be made in detail to the embodiments of the present disclosure with reference to the accompanying drawings. Wherever possible, the same reference numbers will be used throughout the disclosure including the drawings to refer to the same or like parts. As such, the repeatable description of the same or like parts will be omitted.

FIG. 1 is a conceptual diagram of a system for providing a chatbot for rehabilitation education for a hearing loss patient according to an embodiment of the present disclosure.

Referring to FIG. 1, a system 10 for providing the chatbot for rehabilitation education for a hearing loss patient according to an embodiment of the present disclosure may provide a chatbot provision service for rehabilitation education for the hearing loss patient that provides interactive hearing rehabilitation education content to correct speech language cognitive processing of the hearing loss patient (hereinafter, a “chatbot service for hearing loss rehabilitation”).

In an embodiment, the system for providing the chatbot for rehabilitation education for a hearing loss patient that provides the chatbot service for hearing loss rehabilitation may include a terminal 100, a rehabilitation content providing server 200, and a network 300.

In this connection, the terminal 100 and the rehabilitation content providing server 200 may be connected through the network 300.

Herein, the network 300 according to an embodiment refers to a connection structure capable of exchanging information between nodes such as the terminal 100 and/or the rehabilitation content providing server 200. Examples of the network 300 include 3GPP (3rd Generation Partnership Project) network, LTE (Long Term Evolution) network, WIMAX (World Interoperability for Microwave Access) network, Internet, LAN (Local Area Network), Wireless LAN (Wireless Local Area Network), WAN (Wide Area Network), PAN (Personal Area Network), Bluetooth network, Satellite Broadcasting Network, Analog Broadcasting Network, and DMB (Digital Multimedia Broadcasting) network, but are not limited thereto.

Hereinafter, the terminal 100 and the rehabilitation content providing server 200 that implement the system for providing the chatbot for rehabilitation education for a hearing loss patient will be described in detail with reference to the attached drawings.

Terminal 100

The terminal 100 according to an embodiment of the present disclosure may be a predetermined computing device in which a chatbot application for providing the chatbot service for hearing loss rehabilitation is installed.

Specifically, from a hardware point of view, the terminal 100 may include a mobile-type computing device 100-1 and/or a desktop-type computing device 100-2 in which the chatbot application is installed.

Herein, the mobile-type computing device 100-1 may be a mobile device such as a smartphone or tablet PC in which the chatbot application is installed.

For example, the mobile-type computing device 100-1 may include a smartphone, a mobile phone, a digital broadcasting terminal 100, a personal digital assistant (PDA), a portable multimedia player (PMP), and a tablet PC.

In addition, the desktop-type computing device 100-2 may include a device installed with a program to execute the chatbot service for hearing loss rehabilitation based on wired/wireless communication such as a fixed-type desktop PC, a laptop computer, and a personal computer such as an ultrabook in which the chatbot application is installed.

In addition, according to an embodiment, the terminal 100 may further include a predetermined server computing device that provides a chatbot service environment for hearing loss rehabilitation.

Figure 2:
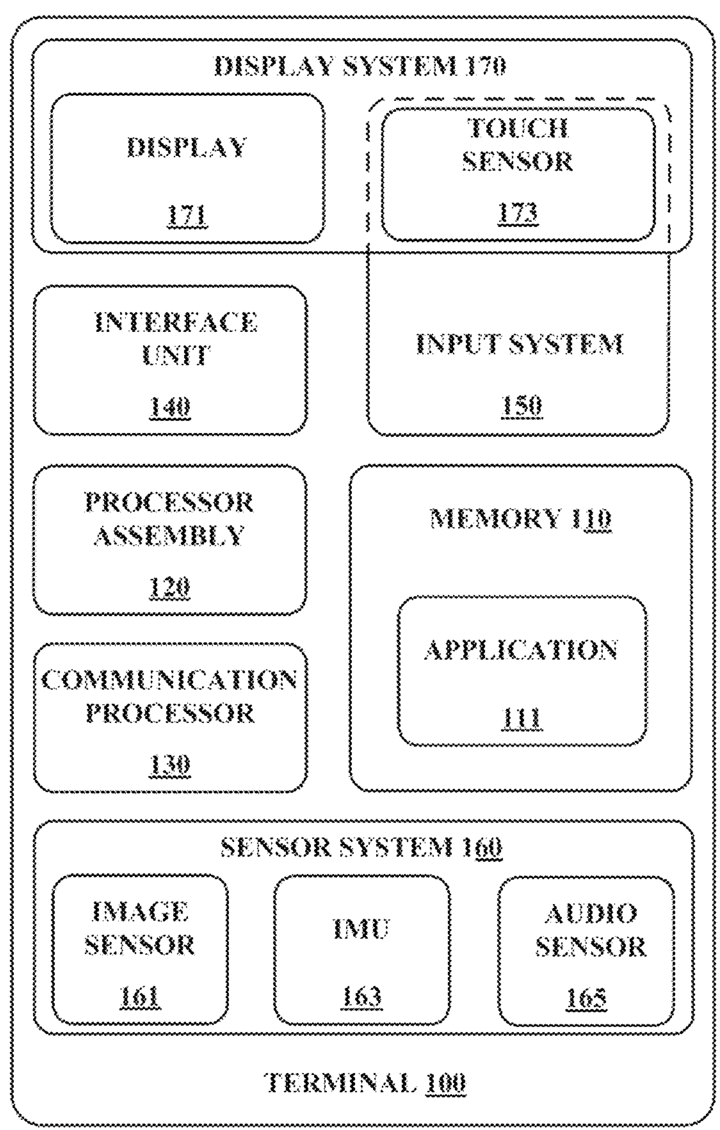
FIG. 2 is an internal block diagram of a terminal according to an embodiment of the present disclosure.

FIG. 2 is an internal block diagram of a terminal according to an embodiment of the present disclosure.

Referring to FIG. 2, from a functional point of view, the terminal 400 may include a memory 110, a processor assembly 120, a communication module 130, an interface module 140, an input system 150, a sensor system 160, and a display system 170. These components may be configured to be included within a housing of the terminal 100.

Specifically, the memory 110 may store the chatbot application 111, and the chatbot application 111 may store one or more of various application programs, data, and instructions for providing the chatbot service environment for hearing loss rehabilitation.

In other words, the memory 110 may store commands and data used for creating the chatbot service environment for hearing loss rehabilitation.

In addition, the memory 110 may include a program area and a data area.

Herein, the program area according to an embodiment may be linked between an operating system (OS) for booting the terminal 100 and functional elements, and the data area may store data generated according to the use of the terminal 100.

In addition, the memory 110 may include at least one non-transitory computer-readable storage medium and a temporary computer-readable storage medium.

For example, the memory 110 may be various storage devices, such as a ROM, an EPROM, a flash drive, and a hard drive; and may be a web storage performing a storage function of the memory 110 on the Internet.

The processor assembly 120 may include at least one processor capable of executing commands of the chatbot application 111 stored in the memory 110 to perform various tasks for creating the chatbot service environment for hearing loss rehabilitation.

In an embodiment, the processor assembly 120 may control the overall operation of components through the chatbot application 111 of the memory 110 in order to provide the chatbot service for hearing loss rehabilitation.

The processor assembly 120 may be a system-on-chip (SOC) suitable for the terminal 100 that includes a central processing unit (CPU) and/or graphics processing unit (GPU), may execute the OS and/or an application program stored in the memory 110, and control each component mounted on the terminal 100.

In addition, the processor assembly 120 may communicate with each component internally through a system bus and may include one or more predetermined bus structures including a local bus.

In addition, the processor assembly 120 may be implemented by using at least one of application-specific integrated circuits (ASICs), digital signal processors (DSPs), digital signal processing devices (DSPDs), programmable logic devices (PLDs), field programmable gate arrays (FPGAs), controllers, micro-controllers, microprocessors, and electric units for performing other functions.

The communication module 130 may include one or more devices for communicating with an external device. The communication module 130 may communicate through a wireless or wired network.

In detail, the communication module 130 may communicate with the terminal 100 storing a content source for providing the chatbot service environment for hearing loss rehabilitation, and may communicate with various user input components such as a controller receiving a user input.

In an embodiment, the communication module 130 may transmit/receive various pieces of data related to the chatbot service for hearing loss rehabilitation to/from another terminal 100 and/or an external server.

This communication module 130 may wirelessly transmit and receive data with at least one of a base station, an external terminal 100, and an arbitrary server on a mobile communication network built through a communication device capable of performing technical standards or communication methods (for example, LTE (Long Term Evolution), LTE-A (Long Term Evolution-Advanced), 5G NR (New Radio), and WIFI) for mobile communication.

The sensor system 160 may include various sensors such as an image sensor 161, a position sensor (IMU) 163, an audio sensor 165, a distance sensor, a proximity sensor, and a contact sensor.

Herein, the image sensor 161 may capture an image and/or a video of a physical space around the terminal 100.

In an embodiment, the image sensor 161 may capture and acquire an image (for example, a user image) related to the chatbot service for hearing loss rehabilitation.

In addition, the image sensor 161 may be disposed on the front or/and rear side of the terminal 100 to acquire an image by capturing the disposed direction side, and may capture a physical space through a camera disposed toward the outside of the terminal 100.

The image sensor 161 may include an image sensor device and a video processing module. Specifically, the image sensor 161 may process a still image or a moving image obtained by an image sensor device (for example, CMOS or CCD).

In addition, the image sensor 161 may process a still image or a moving image obtained through the image sensor device using an image processing module to extract necessary information, and transmit the extracted information to a processor.

The image sensor 161 may be a camera assembly including at least one or more cameras. The camera assembly may include a general camera that captures a visible light band, and may further include a special camera such as an infrared camera or a stereo camera.

In addition, the aforementioned image sensor 161 may be operated while being included in the terminal 100 according to an embodiment, or may be included in an external device (for example, an external server) to operate through interworking based on the aforementioned communication module 130 and/or interface module 140.

The IMU 163 may sense at least one of motion and acceleration of the terminal 100. For example, the IMU 163 may include a combination of various position sensors such as an accelerometer, a gyroscope, and a magnetometer.

In addition, the IMU may interwork with the position communication module 130 such as GPS of the communication module 130 to recognize spatial information on the physical space around the terminal 101.

The audio sensor 165 may recognize a sound around the terminal 100.

In detail, the audio sensor 165 may include a microphone capable of sensing a speech input of a user using the terminal 100.

In an embodiment, the audio sensor 165 may receive speech data necessary for the chatbot service for hearing loss rehabilitation from a user.

The interface module 140 may communicatively connect the terminal 100 with one or more other devices. Specifically, the interface module 140 may include wired and/or wireless communication devices that are compatible with one or more different communication protocols.

The terminal 100 may be connected to various input/output devices through the interface module 140.

For example, the interface module 140 may be connected to an audio output device such as a headset port or a speaker to output audio.

Although it has been described as an example that the audio output device is connected through the interface module 140, an embodiment in which the audio output device is installed in the terminal 100 may also be included.

In addition, for example, the interface module 140 may be connected to an input device such as a keyboard and/or mouse to acquire user input.

Although it has been described as an example that the keyboard and/or mouse is connected through the interface module 140, an embodiment in which the keyboard and/or mouse is installed in the terminal 100 may also be included.

This interface module 140 may include at least one of a wired/wireless headset port, an external charger port, a wired/wireless data port, a memory card port, a port for connecting a device equipped with an identification module, an audio input/output (I/O) port, a video I/O port, an earphone port, a power amplifier, an RF circuit, a transceiver and other communication circuits.

The input system 150 may sense a user input (for example, a gesture, a speech command, operation of a button, or other type of input) related to the chatbot service for hearing loss rehabilitation.

Specifically, the input system 150 may include a predetermined button, a touch sensor, and/or an image sensor 161 that receives a user motion input.

In addition, the input system 150 may be connected to an external controller through the interface module 140 to receive a user input.

The display system 170 may output various pieces of information related to the chatbot service for hearing loss rehabilitation as a graphic image.

In an embodiment, the display system 170 may display a chatbot user interface (UI) for rehabilitation education for a hearing loss patient, hearing loss rehabilitation content, and/or data based on a content management system (CMS).

Such display may include at least one of a liquid crystal display (LCD), a thin film transistor-liquid crystal display (TFT LCD), an organic light-emitting diode (OLED), and a flexible display, a 3D display, and an electronic ink display (e-ink display).

The above components may be disposed within the housing of the terminal 100, and a user interface may include a touch sensor 173 on a display 171 configured to receive a user touch input.

In detail, the display system 170 may include the display 171 that outputs an image and the touch sensor 273 that senses a user touch input.

For example, the display 171 may form an overlaid structure with the touch sensor 173 or integrally formed to be implemented as a touch screen. Such a touch screen may function as a user input unit that provides an input interface between the terminal 100 and the user, and may provide an output interface between the terminal 1000 and the user.

The terminal 100 according to an embodiment of the present disclosure may perform deep learning required for the chatbot service for hearing loss rehabilitation in conjunction with a predetermined deep learning model.

Herein, the deep learning model according to an embodiment may include a speech-to-text (STT) deep learning model, a speech recognition deep learning model, a hidden Markov model (HMM)-based deep learning model, and/or a long short-term memory (LSTM)-based deep learning model.

In addition, according to an embodiment, the terminal 100 may further perform at least a portion of functional operations performed by the rehabilitation content providing server 200, which will be described later.

Rehabilitation Content Providing Server 200

The rehabilitation content providing server 200 according to an embodiment of the present disclosure may perform a series of processes for providing the chatbot service for hearing loss rehabilitation.

In detail, in an embodiment, the rehabilitation content providing server 200 may provide the chatbot service for hearing loss rehabilitation by exchanging data necessary to enable for a chatbot provision process for rehabilitation education for a hearing loss patient to drive in an external device such as the terminal 100 with the external device.

In more detail, in an embodiment, the rehabilitation content providing server 200 may provide an environment in which the chatbot application 111 in an external device (in an embodiment, the mobile-type computing device 100-1 and/or the desktop-type computing device 100-2) may operate.

To this end, the rehabilitation content providing server 200 may include an application programs, data and/or instructions for operating the chatbot application 111, and may transmit/receive data based thereon to/from the external device.

In addition, in an embodiment, the rehabilitation content providing server 200 may execute the chatbot for rehabilitation education for a hearing loss patient that provides hearing loss rehabilitation content.

Herein, the hearing loss rehabilitation content according to an embodiment may be learning content aimed at auditory rehabilitation education to correct speech language cognitive processing of a hearing loss patient.

In addition, in an embodiment, the rehabilitation content providing server 200 may determine the type of hearing loss rehabilitation content on the basis of the executed chatbot for rehabilitation education for a hearing loss patient.

Herein, the type of hearing loss rehabilitation content according to an embodiment may be information that specifies the type of problem provided based on the hearing loss rehabilitation content.

In addition, in an embodiment, the rehabilitation content providing server 200 may provide hearing loss rehabilitation content according to the determined type of hearing loss rehabilitation content to an external terminal (in an embodiment, the terminal 100).

In addition, in an embodiment, the rehabilitation content providing server 200 may acquire user response data based on the provided hearing loss rehabilitation content.

In addition, in an embodiment, the rehabilitation content providing server 200 may execute a correct/wrong processing process based on the acquired user response data.

Herein, in an embodiment, the correct/wrong processing process may refer to a process of determining whether the acquired user response data is a correct answer or a wrong answer.

In addition, in an embodiment, the rehabilitation content providing server 200 may provide the result of the correct/wrong processing based on the hearing loss rehabilitation content.

In addition, in an embodiment, the rehabilitation content providing server 200 may perform user-customized deep learning model learning.

In detail, in an embodiment, the rehabilitation content providing server 200 may perform deep learning required for the chatbot service for hearing loss rehabilitation in conjunction with a predetermined deep learning model.

In more detail, in an embodiment, the rehabilitation content providing server 200 may read a predetermined deep neural network driving program built to perform the deep learning from the memory module 230, and perform deep learning described below according to the read predetermined deep neural network system.

Herein, the deep learning model according to an embodiment may include the STT deep learning model, the speech recognition deep learning model, the HMM-based deep learning model, and/or the LSTM-based deep learning model.

In this connection, in an embodiment, the aforementioned deep learning model is directly included in the rehabilitation content providing server 200, or is implemented as a separate device and/or server from the rehabilitation content providing server 200 to perform deep learning for the chatbot service for hearing loss rehabilitation.

In the following description, the deep learning model is described as being included and implemented in the rehabilitation content providing server 200, but is not limited thereto.

In addition, in an embodiment, the rehabilitation content providing server 200 may train the aforementioned deep learning model as a customized deep learning model optimized for the characteristics of each user (in an embodiment, the utterance characteristics of a user).

In addition, in an embodiment, the rehabilitation content providing server 200 may store and manage various application programs, instructions and/or data for implementing the chatbot service for hearing loss rehabilitation.

In an embodiment, the rehabilitation content providing server 200 may store and manage at least one piece of hearing loss rehabilitation content, type of hearing loss rehabilitation content, user response data, correct/wrong processing result data, and/or a predetermined deep learning model.

Further referring to FIG. 1, in an embodiment, the aforementioned rehabilitation content providing server 200 may be implemented as a predetermined computing device including at least one processor module 210 for data processing, at least one communication module 220 for data exchange with an external device, and at least one memory module 230 that stores various application programs, data, and/or instructions for providing the chatbot service for hearing loss rehabilitation.

Herein, the memory module 230 may store one or more of the OS, various application programs, data, and instructions for providing the chatbot service for hearing loss rehabilitation.

In addition, the memory module 230 may include the program area and the data area.

Herein, the program area according to the embodiment may be linked between the OS for booting a server and functional elements, and the data area may store data generated according to the use of the server.

In an embodiment, the memory module 230 may be various storage devices, such as a ROM, a RAM, an EPROM, a flash drive, and a hard drive, and may be a web storage performing a storage function of the memory module 230 on the Internet.

In addition, the memory module 230 may be a recording medium detachable from the server.

The processor module 210 may control the overall operation of each unit to implement the chatbot service for hearing loss rehabilitation.

The processor module 210 may be the SOC suitable for the server that includes the CPU and/or GPU, may execute the OS and/or an application program stored in the memory module 230, and control each component mounted on the server.

In addition, the processor module 210 may communicate with each component internally through a system bus and may include one or more predetermined bus structures including a local bus.

In addition, the processor module 210 may be implemented by using at least one of the ASICS, DSPs, DSPDs, PLDs, FPGAs, controllers, micro-controllers, microprocessors, and electric units for performing other functions.

In the above description, it has been described that the rehabilitation content providing server 200 according to an embodiment of the present disclosure performs the functional operation as described above. However, according to an embodiment, various embodiments may be possible, such as performing at least a portion of the functional operation performed by the rehabilitation content providing server 200 (for example, the terminal 100), and further performing at least a portion of the functional operation performed in the external device in the rehabilitation content providing server 200.

Method for Providing Chatbot for Rehabilitation Education for Hearing Loss Patient Hereinafter, a method in which the chatbot application 111 executed by at least one or more processors of the terminal 100 according to an embodiment of the present disclosure provides interactive hearing rehabilitation education content to correct speech language cognitive processing of a hearing loss patient will be described in detail with reference to the accompanying FIGS. 3 to 7.

In an embodiment of the present disclosure, at least one or more processors of the terminal 100 may execute at least one or more chatbot applications 111 stored in at least one or more memories 110 or may operate in a background state.

Hereinafter, the at least one or more processors operating to execute the instructions of the chatbot application 111 to perform the method for providing the chatbot service for hearing loss rehabilitation described above will be briefly described as being performed by the chatbot application 111.

Figure 3:
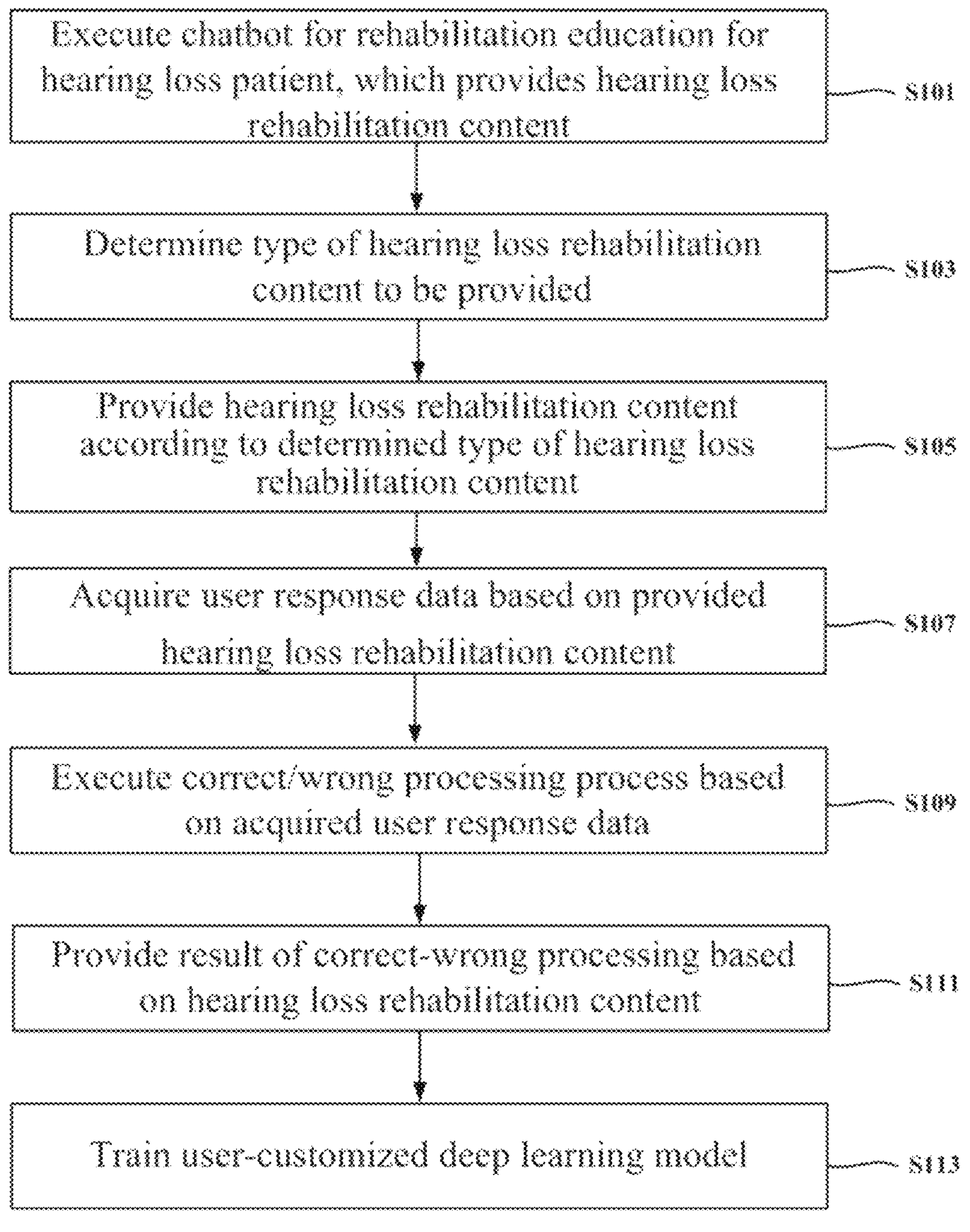
FIG. 3 is a flowchart illustrating a method for providing a chatbot for rehabilitation education for a hearing loss patient according to an embodiment of the present disclosure.

FIG. 3 is a flowchart illustrating a method for providing a chatbot for rehabilitation education for a hearing loss patient according to an embodiment of the present disclosure.

Referring to FIG. 3, in an embodiment, the chatbot application 111, which is executed by at least one processor of the terminal 100 or operates in the background state, may execute the chatbot for rehabilitation education for a hearing loss patient that provides hearing loss rehabilitation content (S101).

Herein, the hearing loss rehabilitation content according to an embodiment may be learning content aimed at auditory rehabilitation education to correct speech language cognitive processing of a hearing loss patient.

In an embodiment, such hearing loss rehabilitation content may include question-and-answer type learning content that provides a problem based on predetermined speech data (hereinafter, an "audio quiz") and acquires a response of a user (in an embodiment, a hearing loss patient) thereto to perform correct/wrong processing.

In other words, in an embodiment, the chatbot application 111 may execute the chatbot for rehabilitation education for a hearing loss patient capable of performing hearing loss rehabilitation education in a conversational manner (in other words, a chat-type program method) with a user (in an embodiment, a hearing loss patient) based on the aforementioned hearing loss rehabilitation content.

In addition, in an embodiment, the chatbot application 111 may determine the type of hearing loss rehabilitation content based on the executed chatbot for rehabilitation education for a hearing loss patient (S103).

Herein, the type of hearing loss rehabilitation content according to an embodiment may be information that specifies the form of problem provided based on the hearing loss rehabilitation content.

In an embodiment, the type of hearing loss rehabilitation content may include a word-type problem type that provides problems in units of predetermined words and/or a sentence-type problem type that provides problems in units of predetermined sentences.

In detail, in an embodiment, the chatbot application 111 may provide a user interface for selecting the type of hearing loss rehabilitation content.

In addition, the chatbot application 111 may determine the type of hearing loss rehabilitation content based on the selection input of a user (in the example, a hearing loss patient) based on the provided user interface.

In addition, in an embodiment, the chatbot application 111 may provide hearing loss rehabilitation content according to the determined type of hearing loss rehabilitation content (S105).

In detail, in an embodiment, the chatbot application 111 may read at least one piece of hearing loss rehabilitation content divided into the determined type of hearing loss rehabilitation content from the memory 110 and/or an external database (for example, the memory module 230 of the rehabilitation content providing server 200). Hereinafter, it will be explained that the hearing loss rehabilitation content is stored and managed based on the memory 110, without being limited thereto.

In addition, the chatbot application 111 may provide the read at least one piece of hearing loss rehabilitation content based on the chatbot for rehabilitation education for a hearing loss patient.

More specifically, in an embodiment, the chatbot application 111 may classify at least one piece of hearing loss rehabilitation content according to a plurality of problem types (in an embodiment, word-type problem type and/or sentence-type problem type) and stores the same in the memory 110.

In addition, in an embodiment, the chatbot application 111 may read at least one piece of hearing loss rehabilitation content included in a type of hearing loss rehabilitation content determined according to an input of a user (in an embodiment, a hearing loss patient) input from the memory 110.

In addition, in an embodiment, the chatbot application 111 may display and output the read hearing loss rehabilitation content based on the chatbot for rehabilitation education for a hearing loss patient.

In this connection, in an embodiment, the chatbot application 111 may provide different types of problems depending on the type of corresponding hearing loss rehabilitation content.

Figure 4:
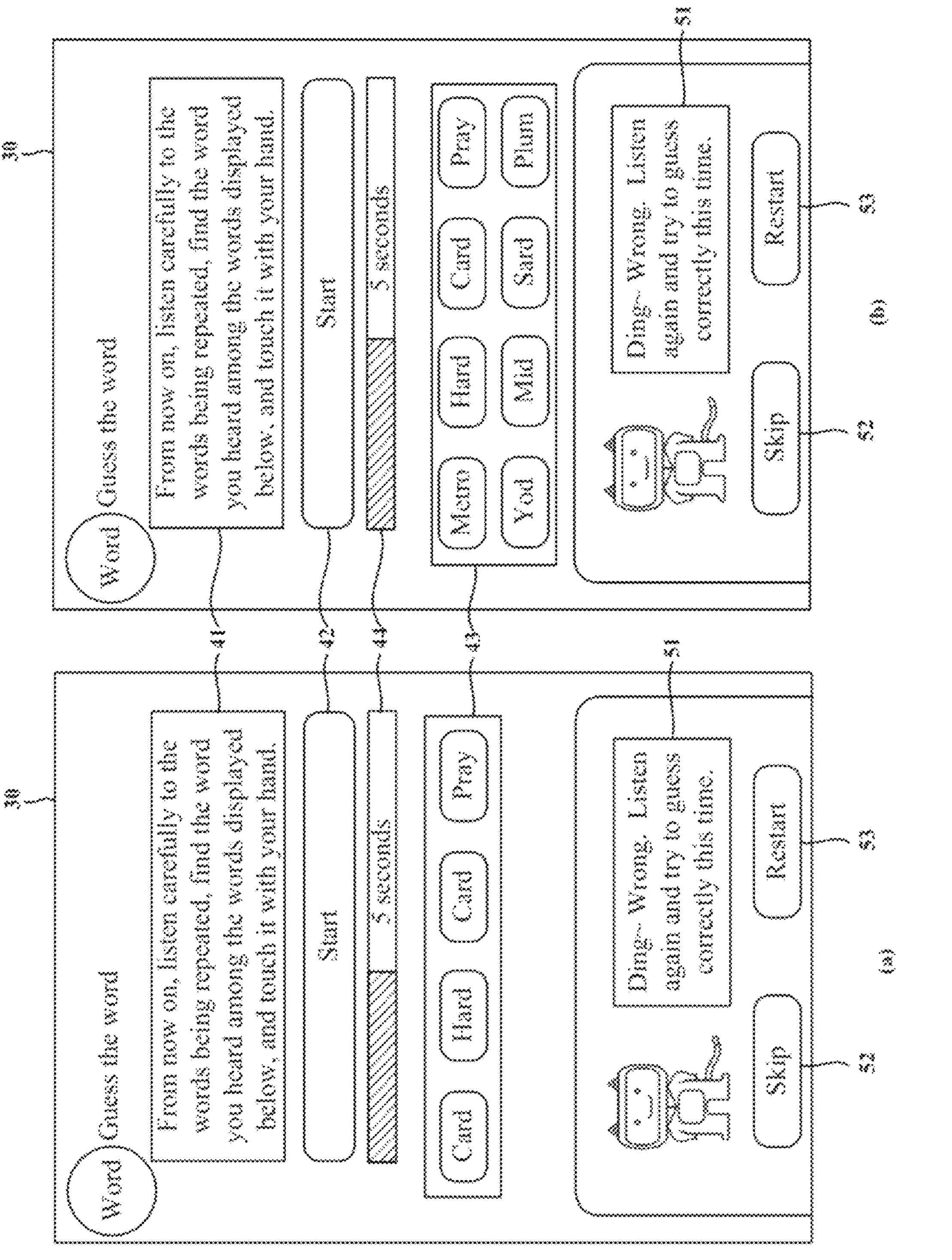
FIG. 4 is an example of a diagram for explaining word-type rehabilitation content according to an embodiment of the present disclosure.

FIG. 4 is an example of a diagram for explaining word-type rehabilitation content according to an embodiment of the present disclosure.

Specifically, referring to FIG. 4, in an embodiment, 1) in the case of hearing loss rehabilitation content that is a word-type problem type (hereinafter, "word-type rehabilitation content 30"), the chatbot application 111 may provide the user interface including a problem guidance text 41, an audio quiz start button 42, and multiple choice selection items 43.

Herein, the problem guidance text 41 according to an embodiment may be a predetermined text explaining a question-and-answer method of the corresponding word-type rehabilitation content 30.

In addition, the audio quiz start button 42 according to an embodiment may be a trigger interface that may output an audio quiz provided by the corresponding word-type rehabilitation content 30 when an input of a user (in an embodiment, a hearing loss patient) for the start button is acquired.

In addition, the multiple choice selection items 43 according to an embodiment may be an answer selection interface that may determine a response of a user (in an embodiment, a hearing loss patient) to the audio quiz as one of a plurality of choices.

For example, the chatbot application 111 may provide the problem guidance text 41 such as "From now on, listen carefully to the words being said repeatedly, find the word you heard among the words displayed below, and touch the same with your hand," the audio quiz start button 42 such as "Get started," and the multiple choice selection items 43 including a plurality of choices such as "Card, hard, sard and prayer."

In addition, in an embodiment, the chatbot application 111 may output a predetermined audio quiz when a user input for the audio quiz start button 42 is acquired.

In this connection, in an embodiment, the chatbot application 111 may change the display to a replay button once the audio quiz start button 42 is selected.

In addition, when the replay button is selected according to the user input, the chatbot application 111 may replay the corresponding audio quiz a predetermined number of times and provide the same.

In addition, in an embodiment, the chatbot application 111 may provide a timer interface 44 that indicates a predetermined time limit (for example, 5 seconds) when the audio quiz is output.

In this connection, in an embodiment, the chatbot application 111 may discriminate whether an input from a user (in an embodiment, a hearing loss patient) selecting at least one of the multiple choice selection items 43 are acquired within the predetermined time limit.

In addition, when the user input is not acquired within the predetermined time limit, the chatbot application 111 may perform a wrong answer processing process described later.

When the user input is acquired within the predetermined time limit, the chatbot application 111 may perform a correct/wrong processing process based on the user choice selected according to the user input among the multiple choice selection items 43.

Herein, the correct/wrong processing process according to an embodiment may refer to a process of determining whether the response input of a user including the selected user choice is a correct answer or a wrong answer. A detailed explanation thereof will be described later in stage S109.

In addition, in an embodiment, the chatbot application 111 may execute the wrong answer processing process when the answer is determined to be wrong as a result of the correct/wrong processing.

In detail, the chatbot application 111 that executes the wrong answer processing process may provide a user interface including a wrong answer guidance text 51, a skip button 52, and a restart button 53.

Herein, the wrong answer guidance text 51 according to an embodiment may be a text explaining that the user choice selected by a user (in an embodiment, a hearing loss patient) is a wrong answer.

For example, the wrong answer guidance text 51 may be predetermined text such as "Wrong. Listen again and try to guess."

In addition, the skip button 52 according to an embodiment may be an interface that may provide the word-type rehabilitation content 30 based on another audio quiz when an input of a user (in an embodiment, a hearing loss patient) for the skip button 52 is acquired.

In this connection, the chatbot application 111 may process the problem as a wrong answer when the skip button 52 is selected.

In addition, the restart button 53 according to an embodiment may be an interface that may additionally perform the audio quiz a predetermined number of times when an input of a user (in an embodiment, a patient with hearing loss) to the restart button 53 is acquired.

In this connection, the chatbot application 111 may restrict further performance based on the restart button 53 when wrong answer processing is performed more than the predetermined number of times.

In addition, when the restart button 53 is selected and the problem is provided again, the chatbot application 111 may rearrange the order of a plurality of choices in the multiple choice selection items 43 that matches the problem.

In an embodiment, the chatbot application 111 may execute a correct answer processing process when it is determined that the answer is wrong as a result of the correct/wrong processing.

In detail, the chatbot application 111 that has executed the correct answer processing process may process the corresponding problem as the correct answer and provide the word-type rehabilitation content 30 based on another audio quiz.

As such, the chatbot application 111 provides hearing loss rehabilitation content that implements a hearing loss rehabilitation education process according to the type of problem desired by a user (in an embodiment, a hearing loss patient)

through a chatbot, so that the user may perform effective hearing loss rehabilitation training anytime, anywhere in a desired learning form.

Herein, further referring to FIG. 4(A), according to an embodiment, the chatbot application 111 may provide the word-type rehabilitation content 30 in a way that provides an audio quiz by repeatedly outputting one piece of speech data a plurality of times, and acquires a response from a user (in an embodiment, a patient with hearing loss) who selects a choice within the multiple choice selection items 43 based on the output single speech data.

For example, the chatbot application 111 may provide an audio quiz by repeating predetermined speech data such as "hard, hard, hard" three times, and may provide, based thereon, the word-type rehabilitation content 30 that acquires a response from a user (in an embodiment, a hearing loss patient) who selects a choice within the multiple choice selection items 43.

Alternatively, further referring to FIG. 4(B), according to an embodiment, the chatbot application 111 may provide the word-type rehabilitation content 30 in a way that provides an audio quiz by sequentially outputting a plurality of different pieces of speech data, and acquires a response from a user (in an embodiment, a hearing loss patient) who selects at least one of a plurality of choices within the multiple choice selection items 43 based on the plurality of pieces of output speech data.

For example, the chatbot application 111 may provide an audio quiz that sequentially outputs predetermined speech data such as "hard, card, guard, mid," and may provide, based thereon, the word-type rehabilitation content 30 that acquires a response from a user (in an embodiment, a hearing loss patient) who selects at least one choice within the multiple choice selection items 43.

As such, the chatbot application 111 may implement a more diversified hearing training process by providing audio quizzes for hearing loss rehabilitation education in various ways even when the problem type is the same.

Figure 5:
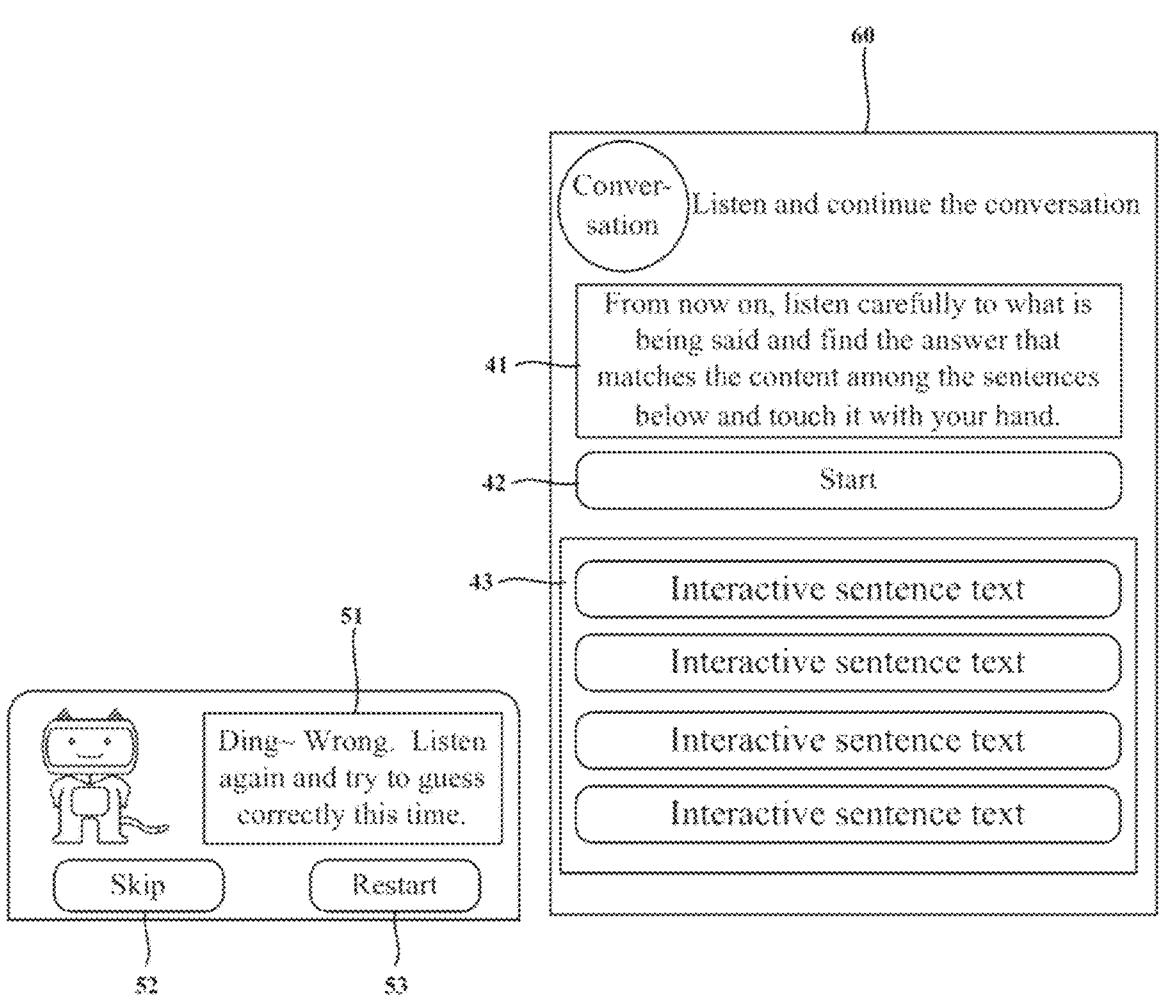
FIG. 5 is an example of a diagram for explaining sentence-type rehabilitation content according to an embodiment of the present disclosure.

FIG. 5 is an example of a diagram for explaining sentence-type rehabilitation content according to an embodiment of the present disclosure.

Referring to FIG. 5, in an embodiment, 2) in the case of hearing loss rehabilitation content that is a sentence-type problem type (hereinafter, "sentence-type rehabilitation content 30"), the chatbot application 111 may provide the user interface including the problem guidance text 41, the audio quiz start button 42, and the multiple choice selection items 43. Hereinafter, content that overlaps with the above description may be summarized or omitted.

For example, the chatbot application 111 may provide the problem guidance text 41 such as "Please listen carefully to what is being said from now on, find the answer that matches the content among the sentences below, and touch the same with your hand," the audio quiz start button 42 such as "Get started," and the multiple choice selection items 43 including a plurality of choices such as "a first interactive sentence text, a second interactive sentence text, a third interactive sentence text, and a fourth interactive sentence text."

In addition, in an embodiment, the chatbot application 111 may output a predetermined audio quiz when a user input for the audio quiz start button 42 is acquired.

In addition, in an embodiment, the chatbot application 111 may provide the timer interface 44 that indicates a predetermined time limit (for example, 5 seconds) when the audio quiz is output.

In addition, when the user input is not acquired within the predetermined time limit, the chatbot application 111 may perform the wrong answer processing process.

When the user input is acquired within the predetermined time limit, the chatbot application 111 may perform a correct/wrong processing process based on the user choice selected according to the user input among the multiple choice selection items 43.

In addition, the chatbot application 111 may execute the wrong answer processing process or the correct answer processing process according to a result of the correct/wrong processing.

As such, the chatbot application 111 provides audio quizzes in the form of sentences according to the selection of a user (in an embodiment, hearing loss patient), thereby systematically training not only word-unit speech cognitive abilities, but also sentence-unit conversational speech cognitive skills, which include inference abilities based on context in conversations exchanged in daily life.

More specifically, in an embodiment, the chatbot application 111 may acquire user response data based on the hearing loss rehabilitation content provided as above (S107).

Herein, the user response data according to an embodiment may refer to response data acquired based on an input of a user (in an embodiment, a hearing loss patient) based on an audio quiz provided based on the hearing loss rehabilitation content.

Figure 6:
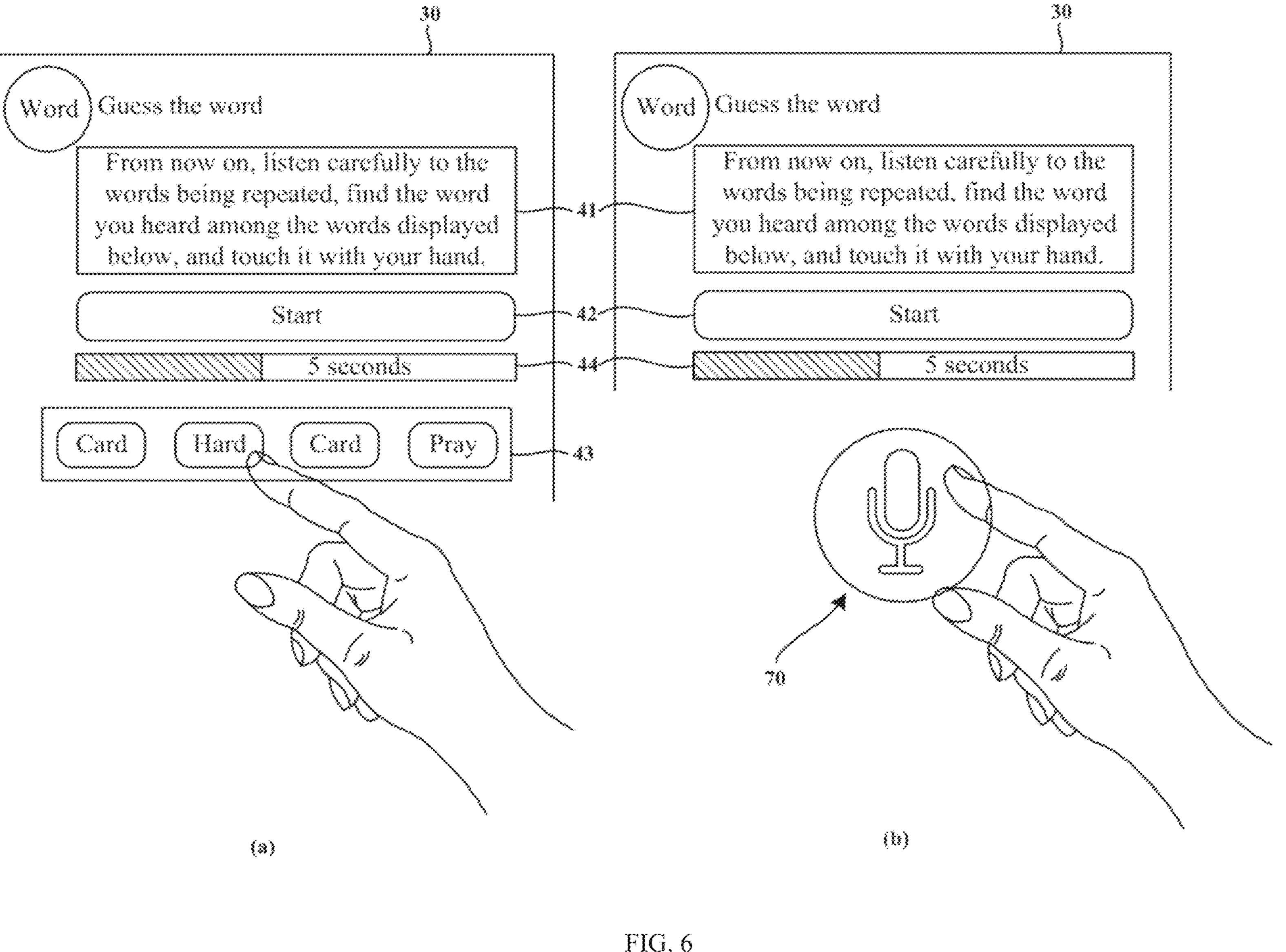
FIG. 6 is an example of a diagram for explaining a method for acquiring user response data according to an embodiment of the present disclosure.

FIG. 6 is an example of a diagram for explaining a method for acquiring user response data according to an embodiment of the present disclosure.

In detail, referring to FIG. 6(A), in an embodiment, the chatbot application 111 may acquire user response data (hereinafter, "user choice input") based on a user input of selecting at least one of the plurality of choices included in the multiple choice selection items 43.

In another embodiment, referring to FIG. 6(B), the chatbot application 111 may acquire user response data (hereinafter, a user speech input) based on a speech input of a user.

In detail, the chatbot application 111 may perform a speech recognition process to acquire a speech input from a user (in an embodiment, a hearing loss patient) after providing the audio quiz described above.

In an embodiment, the chatbot application 111 may provide a speech input user interface 70 capable of performing a speech input and perform a speech recognition process to acquire the user speech input based on the user input.

In this connection, when the corresponding hearing loss rehabilitation content is the word-type rehabilitation content 30 and the acquired user speech input is in the form of a predetermined sentence, the chatbot application 111 may performs natural language processing based on the user speech input in the sentence form to be converted into user speech input in the form of words.

In other words, when a predetermined sentence-type speech input is detected as a response from the user in the word-type rehabilitation content 30 where the user response needs to be in the form of a predetermined word, the chatbot application 111 may convert the detected sentence-type speech input into word-type speech input.

In detail, the chatbot application 111 may filter the acquired sentence-type speech input based on the correct answer data for the word-type rehabilitation content 30.

In an embodiment, the chatbot application 111 may extract speech data corresponding to the correct answer data (hereinafter, "corresponding speech data") from the sentence-type speech input and perform filtering to remove the remaining speech data.

In addition, the chatbot application 111 may convert the sentence-type speech input into the word-type speech input by determining the corresponding speech data filtered and extracted as above to be the user speech input of a user (in an embodiment, a hearing loss patient).

For example, in the case where the sentence-type speech input such as "I think it is OO" is acquired when the hearing loss rehabilitation content is the word-type rehabilitation content 30, the chatbot application 111 may perform natural language processing to extract only "OO" and remove "I think it is" from the sentence-type speech input based on the correct answer data for the word-type rehabilitation content 30. In addition, in this example, the chatbot application 111 may acquire the user speech input by determining the word-type speech input generated through natural language processing as described above as the user speech input of the corresponding user (in an embodiment, a hearing loss patient).

Accordingly, the chatbot application 111 may efficiently refine user response data based on a speech input method and sense the same more accurately.

In addition, in an embodiment, the chatbot application 111 may execute the correct/wrong processing process based on the acquired user response data (S109).

Herein, in other words, the correct/wrong processing process according to an embodiment may refer to a process of determining whether the acquired user response data is a correct answer or a wrong answer.

In detail, in an embodiment, the chatbot application 111 may 1) execute the correct/wrong processing process based on the user choice input.

In more detail, the chatbot application 111 may determine whether the user choice input matches the correct answer data of the corresponding hearing loss rehabilitation content.

In addition, the chatbot application 111 may execute the correct answer processing process when the user choice input and the correct answer data match, and execute the wrong answer processing process when the user choice input and the correct answer data do not match.

For example, the chatbot application 111 may execute the correct answer processing process when the correct answer data of the hearing loss rehabilitation content is "hard" and the user choice input indicates "hard," and may execute the wrong answer processing process in vice versa.

In another embodiment, the chatbot application 111 may 2) execute the correct/wrong processing process based on the user speech input.

In detail, the chatbot application 111 may convert the acquired user speech input into text.

In an embodiment, the chatbot application 111 may use a known deep learning model that converts predetermined speech data into text data (for example, the STT deep learning model) to convert the user speech input into text.

In the following description, for effective explanation, the explanation is based on converting predetermined speech data into text data using the STT deep learning model, without being limited thereto, and this function operation may be performed with any program that includes an algorithm that may convert the predetermined speech data into the text data.

In this connection, the chatbot application 111 may convert the user speech input into a plurality of candidate texts based on the STT deep learning model.

In an embodiment, the chatbot application 111 may convert the user speech input by detecting the plurality of candidate texts having a predetermined similarity rate with the user speech input (in other words, speech data according to the user input).

For example, the chatbot application 111 may detect a first candidate text, a second candidate text, and a third candidate text for a first user speech input and convert the user speech input into the plurality of candidate texts.

In addition, the chatbot application 111 may compare the plurality of candidate texts with the correct answer data of the corresponding hearing loss rehabilitation content to determine whether the answer is correct.

In an embodiment, the chatbot application 111 may execute the correct answer processing process when one of the plurality of candidate texts matches the correct answer data.

The chatbot application 111 may execute the wrong answer processing process when all of the plurality of candidate texts and the correct answer data do not match.

As such, the chatbot application 111 uses a method optimized for each input format to determine whether the user choice input and/or the user speech input representing the response to the corresponding audio quiz is a correct answer, thereby efficiently and more accurately operating a process to determine whether the answer is correct and simultaneously improving the quality of hearing loss rehabilitation education services by utilizing the determination results in a variety of ways in the future.

In this connection, in an embodiment, the chatbot application 111 may execute a recognition error sensing process based on a matching rate between each of the plurality of candidate texts and the correct answer data when all of the plurality of candidate texts and the correct answer data do not match.

Herein, the recognition error sensing process according to an embodiment may refer to a process of checking the user speech input to minimize sensing errors for the user speech input when the correct/wrong processing process is performed based on the user speech input.

Figure 7:
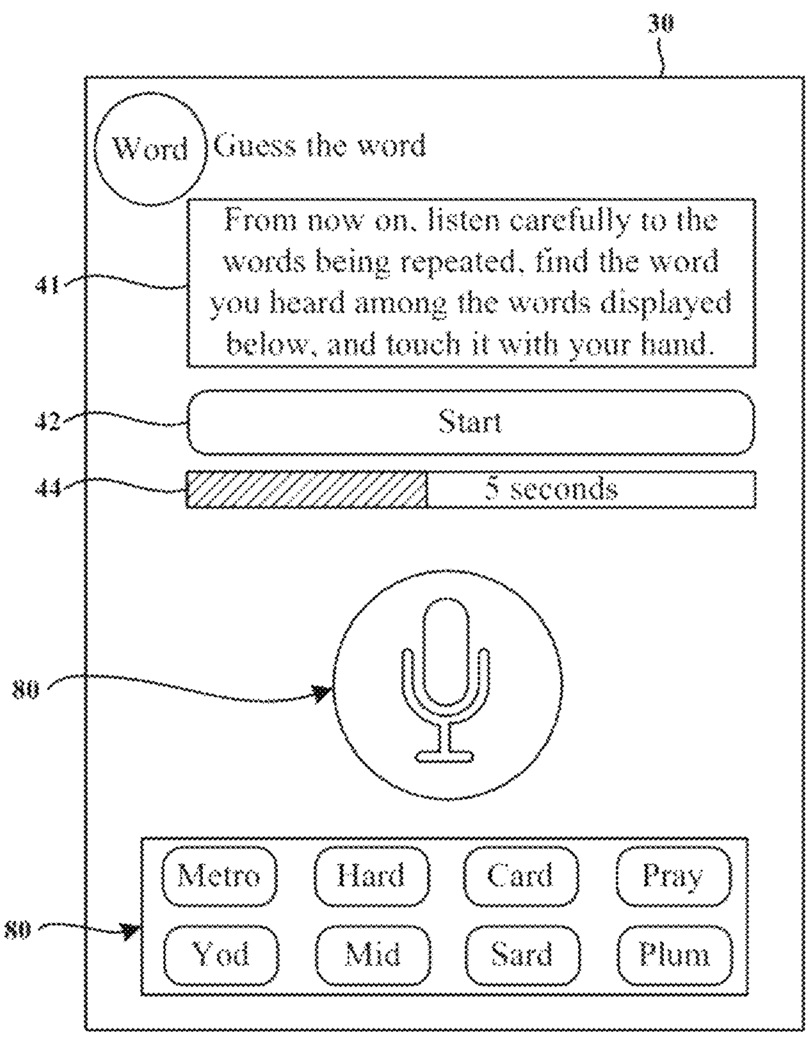
FIG. 7 is an example of a diagram for explaining a cognitive error sensing process according to an embodiment of the present disclosure.

FIG. 7 is an example of a diagram for explaining a cognitive error sensing process according to an embodiment of the present disclosure.

In detail, referring to FIG. 7, in an embodiment, when the matching rate of at least one of the plurality of candidate texts with the correct data meets a predetermined standard value or higher, the chatbot application 111 may provide a my-input selection item 80 based on the corresponding hearing loss rehabilitation content.

In this connection, in an embodiment, the chatbot application 111 may acquire the matching rate using a known deep learning algorithm (for example, a text classification deep learning algorithm based on a Softmax function) that outputs the matching rate between texts.

In addition, herein, the my-input selection item 80 according to an embodiment may be a user interface that allows a user (in an embodiment, a hearing loss patient) to determine what the user speech input was to input as one of a plurality of text-based choices.

In other words, in an embodiment, the chatbot application 111 may query a user (in an embodiment, a patient with hearing loss) to select what text the speech data pronounced and input means based on the my-input selection item 80 and acquire a response thereto.

In this connection, in an embodiment, the chatbot application 111 may provide the choice based on the plurality of texts based on at least one of a main candidate text having a matching rate of more than a predetermined standard value with the correct answer data among the plurality of candidate texts, a correct answer text based on the above answer data, or additional texts generated based on the main candidate text and the correct answer text and remaining candidate texts other than the main candidate text.

Herein, the chatbot application 111 may, for example, generate the additional text based on a deep learning model that uses the main candidate text and the correct answer text as input and uses a predetermined text with a predetermined similarity to the texts as output.

For example, when the main candidate text is "odd," the correct answer text is "hard," and the remaining candidate text is "card, guard, and mod," the chatbot application 111 may generate additional texts including "yard" based on the main candidate text and the correct answer text, and provide the generated additional text, the main candidate text, the correct answer text, and the remaining candidate text as the choice based on the plurality of texts through the my-input selection item 80.

In addition, in an embodiment, the chatbot application 111 may acquire an input of a user (in an embodiment, a patient with hearing loss) who selects at least one of at least one text-based choice in the my-input selection item 80.

In addition, the chatbot application 111 executes the correct answer processing process when the text-based choice selected according to the acquired user input and the corresponding correct answer data match, and executes the wrong answer processing process when the user choice input and the correct answer data do not match.

Accordingly, the chatbot application 111 may minimize sensing errors for user response data acquired based on a speech input method, thereby improving the accuracy of the correct/wrong processing process and enhancing the reliability of the correct/wrong processing results provided later.

In addition, in an embodiment, the chatbot application 111 may provide a correct/wrong processing result based on the hearing loss rehabilitation content (S111).

In detail, in an embodiment, the chatbot application 111 may display and output the results of the correct/wrong processing process based on the hearing loss rehabilitation content performed as described above according to a predetermined method.

In more detail, in an embodiment, the chatbot application 111 may manage the determination of whether a user has a correct answer to the audio quiz provided through the hearing loss rehabilitation content, user response data and/or correct answer data based on the CMS.

In addition, the chatbot application 111 may display and provide data managed based on the CMS in various forms (for example, graphs, tables, charts, and/or report formats, etc.).

Accordingly, the chatbot application 111 may provide visualized data that allows a user (in an embodiment, a hearing loss patient) to easily and intuitively understand the results of hearing loss rehabilitation training performed.

In addition, in an embodiment, the chatbot application 111 may perform user-customized deep learning model learning (S113).

In detail, in an embodiment, the chatbot application 111 may train the STT deep learning model, which converts the user speech input into text and senses the same, to be optimized for the speech input characteristics of a user based on the aforementioned hearing loss rehabilitation content and certain data acquired in the process of performing hearing rehabilitation education for the user (in an embodiment, a hearing loss patient).

In other words, the chatbot application 111 may train the STT deep learning model to be implemented as a user-customized STT deep learning model that may convert speech input by a user into text by considering the pronunciation characteristics of the user (in an embodiment, a hearing loss patient) to which the STT deep learning model corresponds.

In more detail, in an embodiment, the chatbot application 111 may generate a first training data set by mutual matching of candidate text (hereinafter, "correct answer candidate text") that matches the aforementioned correct answer data among the plurality of pieces of candidate text described above, and user speech input data corresponding to the correct answer candidate text.

In addition, in an embodiment, the chatbot application 111 may generate a second training data set by mutual matching of the user speech input data corresponding to a correct text choice and a text-based option (hereinafter, a "correct answer text choice") selected according to an input of the user (in an embodiment, a hearing loss patient) among the plurality of text-based choices in the aforementioned my-input selection item 80.

In addition, in an embodiment, the chatbot application 111 may train the STT deep learning model to optimize the pronunciation characteristics of the user (in an embodiment, a hearing loss patient) based on the first training data set and/or the second training data set generated as above.

In other words, the chatbot application 111 may train the user-customized STT deep learning model based on at least one training data set that pairs user speech input (in other words, speech data according to user input) and corresponding text data.

Thus, the chatbot application 111 may build and utilize the STT deep learning model that may accurately convert the user speech data into text data matching the same by considering the pronunciation characteristics of each user (in an embodiment, a hearing loss patient) in more detail.

In addition, the chatbot application 111 performs speech response recognition for a user (in an embodiment, a hearing loss patient) using the trained STT deep learning model customized to the user, thereby further improving the sensing accuracy of user response data based on speech input and also enhancing the performance of the hearing loss rehabilitation chatbot service.

As described above, the method and system for providing a chatbot for rehabilitation education for a hearing loss patient according to an embodiment of the present disclosure implement a chatbot for rehabilitation education for the hearing loss patient that provides interactive hearing rehabilitation education content to correct speech language cognitive processing of the hearing loss patient, thereby providing an easy hearing loss rehabilitation education process anytime, anywhere in an interactive manner optimized for hearing loss rehabilitation education.

Method for Providing Customized Online Education Content for Rehabilitation for Hearing Loss Patient The chatbot application 111 according to an embodiment of the present disclosure provides the hearing loss rehabilitation content provided to correct speech language cognitive processing of a hearing loss patient in a customized manner to the corresponding user (in other words, a hearing loss patient), as described above, thereby improving the learning effect of the hearing loss rehabilitation education.

Hereinafter, a method in which the chatbot application 111 according to an embodiment of the present disclosure provides online education content for rehabilitation customized to a hearing loss patient based on learning result data based on interactive hearing rehabilitation education content will be described in detail with reference to the attached drawings.

Figure 8:
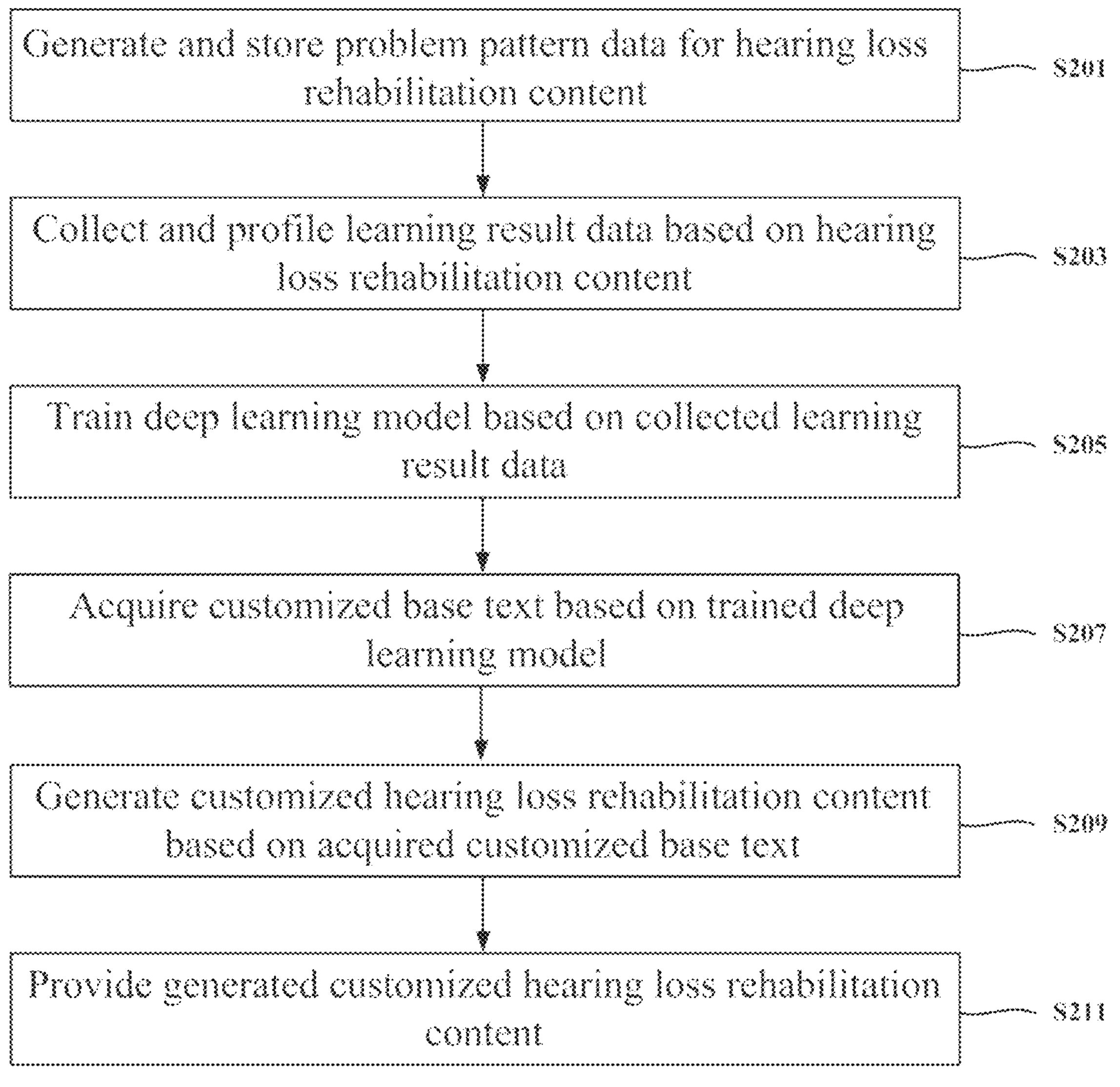
FIG. 8 is a flowchart illustrating a method for providing online education content for rehabilitation customized for a hearing loss patient according to an embodiment of the present disclosure.

FIG. 8 is a flowchart illustrating a method for providing online education content for rehabilitation customized for a hearing loss patient according to an embodiment of the present disclosure.

Referring to FIG. 8, in an embodiment of the present disclosure, the chatbot application 111 may generate and store problem pattern data for the hearing loss rehabilitation content described above (S201).

Herein, the problem pattern data according to an embodiment is data that provides unique attribute information related to the problem provided through the hearing loss rehabilitation content. In an embodiment, the problem pattern data may include a content identification code, base text, and base text analysis data (hereinafter, "analysis data") for the corresponding hearing loss rehabilitation content.

In this connection, the content identification code according to an embodiment may refer to unique identification data (for example, content ID) that specifies predetermined hearing loss rehabilitation content.

In addition, the base text according to an embodiment may refer to text data that serves as the basis for forming an audio quiz provided based on predetermined hearing loss rehabilitation content.

In addition, the analysis data according to an embodiment is data that analyzes the structure of the base text, and may include a morpheme analysis corpus list that is result data according to morpheme analysis of the base text, and grapheme separation data that is result data according to grapheme separation analysis of a morpheme analysis corpus.

In an embodiment, such problem pattern data may be stored and managed by matching the same with corresponding hearing loss rehabilitation content.

In detail, in other words, the hearing loss rehabilitation content according to an embodiment is learning content aimed at hearing rehabilitation education to correct speech language cognitive processing of a hearing loss patient, and may include a content identification code (for example, content ID) that specifies the corresponding hearing loss rehabilitation content, an audio quiz provided based on predetermined audio data, and base text, which is text data on which the audio quiz is formed.

In addition, in an embodiment, the chatbot application 111 may perform structural analysis on the base text of the hearing loss rehabilitation content.

In more detail, in an embodiment, the chatbot application 111 may perform morpheme analysis on the base text in conjunction with a predetermined morphological analyzer.

Herein, the morpheme analysis according to an embodiment refers to a process of segmenting a predetermined text including words and/or sentences, which are linguistic units larger than morphemes, into morphemes, which are the minimum semantic units, and matching part-of-speech information for each segmented morpheme to be transformed into a 'morpheme+part-of-speech information' form.

In this connection, in an embodiment of the present disclosure, the chatbot application 111 may perform the morpheme analysis described above in conjunction with at least one of various known types of morpheme analyzers. In an embodiment of the present disclosure, the morpheme analyzer itself is not limited or restricted.

In addition, in an embodiment, the chatbot application 111 may acquire the morpheme analysis corpus list as result data of morpheme analysis of the base text.

For example, when the first base text is "A resident registration card is required to issue a card," the chatbot application 111 may perform morpheme analysis on the first base text to acquire a first morpheme analysis corpus list including a plurality of segmented morphemes such as "A resident/registration card/is/required/to/issue/a/card" and part-of-speech information for each of the plurality of morphemes.

In addition, in an embodiment, the chatbot application 111 may acquire the grapheme separation data for the base text based on the morpheme analysis corpus list.

In detail, the chatbot application 111 may perform grapheme separation analysis on the morpheme analysis corpus list in conjunction with a predetermined grapheme separation analyzer.

Herein, the grapheme separation analysis according to an embodiment refers to a process of separating each of the segmented morphemes into phoneme units, that is, consonants or vowels, and transforming the same into a role according to the position of separated consonants or vowels, that is, a form that matches any one of the initial consonant, vowel, or final consonant.

In this connection, in an embodiment of the present disclosure, the chatbot application 111 may perform grapheme the separation analysis as described above in conjunction with at least one of various known types of grapheme separation analyzers. In an embodiment of the present disclosure, the grapheme separation analyzer itself is not limited or restricted.

For example, the chatbot application 111 may perform the grapheme separation analysis on the first morpheme analysis corpus list to acquire first grapheme separation data including a plurality of grapheme-separated morphemes such as "(i s), . . . , (to), (i s s u e), (a), (c a r d)" and positional information (in other words, initial consonant, vowel, or final consonant) for each of the grapheme-separated consonants or vowels.

In other words, in an embodiment, the chatbot application 111 generates and stores problem pattern data for each piece of the hearing loss rehabilitation content on the hearing loss rehabilitation education service as described above, thereby building a problem pattern database based on problem pattern data of a plurality of pieces of hearing loss rehabilitation content.

In addition, in an embodiment, the chatbot application 111 may collect and profile learning result data based on the hearing loss rehabilitation content (S203).

Herein, the learning result data according to an embodiment is data providing result information of hearing loss rehabilitation education performed using the hearing loss rehabilitation content, and may refer to the result data of the hearing loss rehabilitation education acquired as a user (in an embodiment, a hearing loss patient) responds to an audio quiz provided through the hearing loss rehabilitation content and correct/wrong processing is executed accordingly.

Specifically, in an embodiment, this learning result data may include a user identification code, unique identification data (for example, a user ID) that specifies the corresponding user (in an embodiment, a hearing loss patient), problem pattern data for the corresponding hearing loss rehabilitation content, correct/wrong processing result data indicating whether there is a correct answer to the audio quiz provided through the corresponding hearing loss rehabilitation content, and user response data according to user input for each of the audio quizzes.

In this connection, in an embodiment, the learning result data may be formed by including at least one problem pattern data, at least one correct/wrong processing result data, and at least one user response data matching a user identification code (for example, a first hearing loss patient identification code).

In detail, in an embodiment, as described in the aforementioned method for providing online education content for rehabilitation for a hearing loss patient, the chatbot application 111 may provide the hearing loss rehabilitation content to a user, acquire user response data for the provided hearing loss rehabilitation content, and execute a correct/wrong processing process based on the acquired user response data.

In this connection, the chatbot application 111 may collect and profile a plurality of pieces of learning result data as the user (in an embodiment, a hearing loss patient) performs rehabilitation education based on hearing loss rehabilitation content according to the aforementioned process.

For example, as the first user performs rehabilitation education based on a plurality of pieces of hearing loss rehabilitation content, the chatbot application 111 may collect and profile the plurality of pieces of learning result data formed in the form of 'first user identification code/identification code for a plurality of pieces of content/text based on a plurality of pieces of content/analysis data for a plurality of pieces of content/correct/wrong processing result data for a plurality of pieces of content, and user response data for a plurality of pieces of content.

In addition, in an embodiment, the chatbot application 111 may train a deep learning model based on the collected learning result data (S205).

In detail, in an embodiment, the chatbot application 111 may use the plurality of pieces of learning result data for a user (in an embodiment, a hearing loss patient) collected as above as a training data set, and train a correct answer learning model and/or a wrong answer learning model according to an embodiment of the present disclosure a customized way for a user (in an embodiment, a hearing loss patient).

Herein, the correct answer learning model according to an embodiment may refer to a deep learning model that outputs correct answer pattern information that provides text structure arrangement information and grapheme combination structure information based on the text when a predetermined text is input, and correct answer probability information that provides the probability that a user (in an embodiment, a hearing loss patient) will correctly answer an audio quiz based on the corresponding text.

In addition, the wrong answer learning model according to an embodiment may refer to a deep learning model that outputs wrong answer pattern information, which is information that models the result value of analyzing the type of wrong answer of a user (in an embodiment, a hearing loss patient) by grapheme based on the text structure arrangement information and grapheme combination structure information based on the text when a predetermined text is input, and wrong answer probability information that provides the probability that a user (in an embodiment, a hearing loss patient) will incorrectly answer an audio quiz based on the corresponding text.

In detail, in an embodiment, the chatbot application 111 may divide the plurality of pieces of collected learning result data into correct answer type content or wrong answer type content.

In more detail, the chatbot application 111 may divide the learning result data into the correct answer type content based on the correct answer processing result data for each piece of the learning result data when the correct/wrong processing result data is an 'correct answer,' and divide the learning result data into the wrong answer type content when the correct/wrong processing result data is a 'wrong answer.'

In addition, in an embodiment, the chatbot application 111 may train the correct answer learning model based on the correct answer type content.

In detail, the chatbot application 111 may train the correct answer learning model based on the base text (hereinafter, "correct answer text") of the correct answer type content.

In more detail, the chatbot application 111 may train the correct answer learning model using a correct answer data set including a plurality of pieces of correct answer text as input data.

In addition, the chatbot application 111 may acquire correct answer pattern information and correct answer probability information based on the plurality of pieces of correct answer text of the corresponding user (in an embodiment, a hearing loss patient) as a result of the training performed as above.

In other words, the chatbot application 111 may acquire the correct answer pattern information and the correct answer probability information specialized for each user as a result of training on the correct answer learning model.

Thus, the chatbot application 111 may perform a verification process on the customized base text generated to have a grapheme combination structure with a high probability of being wrong by a user (in an embodiment, a hearing loss patient) described later in stage S209. A detailed explanation thereof will be provided later.

In an embodiment, the chatbot application 111 may train the wrong answer learning model based on the wrong answer type content.

In detail, the chatbot application 111 may train the wrong answer learning model based on the base text (hereinafter, "wrong answer text") of the wrong answer type content.

Specifically, the chatbot application 111 may train the wrong answer learning model using a wrong answer data set including a plurality of pieces of wrong answer text as input data.

In addition, the chatbot application 111 may acquire the wrong answer pattern information and the wrong answer probability information based on the plurality of pieces of wrong answer text of the user (in an embodiment, a hearing loss patient) as a result of the training performed as above.

In other words, the chatbot application 111 may acquire the wrong answer pattern information and the wrong answer probability information specialized for each user as a result of training on the wrong answer learning model.

Exemplarily, the wrong answer learning model may acquire the wrong answer pattern information by comparing grapheme separation data matching the wrong answer text of a first wrong answer type content (in other words, the base text of the corresponding hearing loss rehabilitation content) with grapheme separation response data acquired by grapheme-separating the user response data of the first wrong answer type content.

For example, when the wrong answer text of the first wrong answer type content is 'simply' and the grapheme separation data matching the wrong answer text is 's i m p l y', and the grapheme separation response of the first wrong answer type content is 'd i m p l y,' the wrong answer learning model may acquire the wrong answer pattern information indicating that 's' is misrecognized as 'd.' Alternatively, as an example, the wrong answer learning model may acquire the wrong answer pattern information by analyzing the consonant and/or vowel arrangement of grapheme separation data that matches the wrong answer text of the first wrong answer type content.

For example, when similarity in speech (or phonetic value) waveform is detected by analyzing the grapheme separation data as above, such as when the neutral vowel following the initial consonant is the same or has the same phonetic value or when the final consonant is the same, the wrong answer learning model may acquire wrong answer pattern information indicating misrecognition when there is a consonant and/or vowel arrangement according to the corresponding case.

As another example, when the grapheme separation data is 's i m p l y' and the grapheme separation response data is 'd i m p l y,' the wrong answer learning model may acquire the wrong answer pattern information indicating misrecognition when there is a consonant and/or vowel arrangement in the form of 's+i.'

In this connection, in this example, the wrong answer learning model may repeatedly perform the aforementioned process for a plurality of pieces of wrong answer type content, and thus may acquire a plurality of pieces of wrong answer pattern information.

Alternatively, in this example, the wrong answer learning model may update the acquired wrong answer pattern information by repeatedly performing the aforementioned process for the plurality of pieces of wrong answer type content.

In addition, in this example, the wrong answer learning model may acquire the wrong answer probability information for each of the plurality of pieces of wrong answer text based on the wrong answer pattern information acquired as above.

For example, the wrong answer learning model may acquire the wrong answer probability information for first wrong answer text in a way such as increasing wrong answer probability as the more the first wrong answer text corresponds to at least some of the plurality of pieces of wrong answer pattern information, and in the opposite case, decreasing the wrong answer probability.

In addition, in this example, the wrong answer learning model may provide wrong answer pattern information and wrong answer probability information acquired as above as output data.

As such, the chatbot application 111 trains the correct answer learning model and the wrong answer learning model using learning result data collected for each user (in an embodiment, a hearing loss patient), thereby building a customized DB specialized for each user, such as correct answer pattern information that the user is likely to get correct and wrong answer pattern information that the user is likely to get wrong.

In addition, the chatbot application 111 trains the wrong answer learning model as described above, and later uses the wrong answer pattern information and/or wrong answer probability information output from the wrong answer learning model as base data, thereby generating a type of user-customized problem (in other words, an audio quiz utilizing user-customized based text in an embodiment) that is determined to have a high probability of being wrong by the user (in an embodiment, a hearing loss patient).

In addition, in an embodiment, the chatbot application 111 may acquire customized base text based on the deep learning model trained as above (S207).

Herein, the customized base text according to an embodiment may refer to predetermined text generated based on the aforementioned wrong answer pattern information to have a form in which the probability of a user (in an embodiment, a hearing loss patient) being wrong is determined to be higher than a predetermined standard.

In other words, in an embodiment, the chatbot application 111 may acquire a corpus of consonant and/or vowel combinations in which the wrong answer probability of a user (in an embodiment, a hearing loss patient) is higher than a predetermined standard based on the wrong answer pattern information about the user, and customized base text including words and/or sentences based on the corpus.

In detail, in an embodiment, the chatbot application 111 may acquire the customized base text based on the wrong answer pattern information in conjunction with a predetermined text generation model.

In more detail, the chatbot application 111 and/or the text generation model may analyze the forward and backward connection structural relationships between consonants and/or vowels of the wrong answer pattern information and generate a database.

In addition, the text generation model, in conjunction with a predetermined text deep learning model, may connect at least one piece of arbitrary text (for example, at least one piece of text among a plurality of pieces of text presently stored in a predetermined dictionary database) based on the forward and backward connection structural relationship to generate and provide the customized base text.

Herein, the text deep learning model may be a predetermined deep learning model that is trained based on a learning data set including a predetermined morpheme analysis corpus list, grapheme separation data, and/or spacing rule logic, and provides customized base text as output data based on methods such as LSTM/RNN. However, in an embodiment of the present disclosure, the text deep learning model itself is not limited or restricted.

For example, when the wrong answer pattern information is based on predetermined daily vocabulary text related to a 'card,' the text generation model may provide customized base text, such as:

'To/issue/a card/a/resident/registration/card/is/required.',
'You/must/bring/your/resident/registration card/to/issue/a card.',
'You/need/a/cell/phone/case/to/store/your/card.', or
'You/need/a/transportation/card/to/ride/the/subway.'

Hereinbefore, it has been explained that the chatbot application 111 may generate the customized base text in conjunction with the text generation model that operates as described above, but this is merely an example and is not limited thereto. The aforementioned functional operations may be performed in conjunction with any model that may implement an algorithm that uses predetermined text pattern information as input data and predetermined text generated according to the text pattern information as output data.

In this connection, in an embodiment, the chatbot application 111 may acquire customized base text according to various types of hearing loss rehabilitation content (in an embodiment, word-type problem type and/or sentence-type problem type) in conjunction with the text generation model.

As such, the chatbot application 111 acquires customized base text in a form in which a user (in an embodiment, a hearing loss patient) is determined to have a high probability of being wrong based on the aforementioned wrong answer pattern information, thereby generating and providing an audio quiz based on a base text having a type that is vulnerable to a user in the future (for example, a consonant-vowel arrangement structure and/or a corpus that is vulnerable to a user), and implementing the hearing loss rehabilitation education service with a form and level of difficulty optimized for the user.

In addition, in an embodiment, the chatbot application 111 may generate customized hearing loss rehabilitation content based on the acquired customized base text (S209).

Herein, the customized hearing loss rehabilitation content according to an embodiment may refer to hearing loss rehabilitation content that provides an audio quiz (hereinafter, a "customized audio quiz") generated based on the customized base text acquired as described above.

In detail, in an embodiment, the chatbot application 111 may perform a verification process for the customized base text.

Herein, the verification process according to an embodiment may refer to a process of identifying whether the customized base text is truly text in which a user is highly likely to get wrong.

In more detail, the chatbot application 111 may perform the verification process based on the correct answer learning model described above.

Specifically, the chatbot application 111 may input the customized base text into the correct answer learning model.

In addition, the chatbot application 111 may acquire the correct answer probability information for the customized base text from the correct answer learning model that receives the customized base text.

In this connection, the chatbot application 111 may generate a customized audio quiz based on the corresponding customized base text when the acquired correct answer probability information is less than a predetermined probability.

In addition, the chatbot application 111 may generate the customized hearing loss rehabilitation content that provides the generated customized audio quiz.

As such, the chatbot application 111 inputs the customized base text generated based on the wrong answer pattern information of a user into the correct answer learning model to predict the probability of correct answer of the user for the customized base text, and generates the customized hearing loss rehabilitation content according to the customized base text only when the predicted probability of correct answer is a predetermined standard value or less, thereby filtering only the customized base text that has been verified to have a high probability of being truly wrong by the user to provide customized rehabilitation content based thereon, and performing hearing loss rehabilitation education more optimized for the level of the user.

In addition, in an embodiment, the chatbot application 111 may provide the generated customized hearing loss rehabilitation content (S211).

In an embodiment, the chatbot application 111 may provide customized hearing loss rehabilitation content 90 generated as above to a user (in an embodiment, a hearing loss patient) through the chatbot for rehabilitation education for a hearing loss patient described above.

In addition, in an embodiment, the chatbot application 111 may collect and profile learning result data based on the provided customized hearing loss rehabilitation content 90, and repeat a process of providing online education content for rehabilitation customized for a user described above based thereon.

Accordingly, the chatbot application 111 may automatically generate and provide problems (in an embodiment, an audio quiz) in hearing loss rehabilitation content provided for the hearing loss rehabilitation education of a user (in an embodiment, a hearing loss patient) so as to have an optimized form and difficulty level according to the miscognition characteristics or degree of hearing loss of the user, and may implement a customized hearing loss rehabilitation education service specialized for each user.

As described above, the method and system for providing online education content for rehabilitation for a hearing loss patient according to an embodiment of the present disclosure provide the online education content for rehabilitation for a hearing loss patient customized for a user based on the learning result data of the user based on interactive hearing rehabilitation education content, thereby providing a hearing loss rehabilitation education process optimized for each user's hearing ability level or characteristics.

INDUSTRIAL APPLICABILITY

The present disclosure is directed to a method for providing a hearing loss rehabilitation education process in which a processor of a terminal controls and provides a program, and thus has industrial applicability.

What is claimed is:

1. A method by which a chatbot application executed by at least one processor of a terminal provides a chatbot for rehabilitation education for a hearing loss patient, the method comprising:

executing the chatbot that provides hearing loss rehabilitation content that is interactive learning content for hearing rehabilitation education for the hearing loss patient;

providing a sentence-type rehabilitation content in the hearing loss rehabilitation content on the basis of the executed chatbot;

acquiring user response data regarding an audio quiz of the provided sentence-type rehabilitation content;

performing a correct/wrong processing process for determining whether or not the acquired user response data is a correct answer;

collecting and profiling learning result data obtained through the correct/wrong processing process;

training a wrong answer learning model based on the collected learning result data to output wrong answer pattern information;

training a correct answer learning model based on the collected learning result data to output correct answer probability information;

generating a customized base text by inputting the wrong answer pattern information into a text generation model;

performing a computer-implemented verification process on the generated customized base text prior to providing the content to the user, wherein the verification process comprises:

inputting the generated customized base text into the trained correct answer learning model, calculating a correct answer probability for the generated customized base text, and determining the generated customized base text as verified content only when the calculated correct answer probability is less than a predetermined threshold;

generating customized hearing loss rehabilitation content based on the verified customized base text; and providing the customized hearing loss rehabilitation content to the user, wherein the acquisition of the user response data comprises generating and storing problem pattern data for the sentence-type rehabilitation content.

2. The method of claim 1, wherein the sentence-type rehabilitation content is question-and-answer type learning content that asks questions based on the audio quiz.

3. The method of claim 1, wherein the provision of the sentence-type rehabilitation content comprises outputting the audio quiz a predetermined number of times based on a sentence, and wherein the acquisition of the user response data comprises acquiring single user response data.

4. The method of claim 1, wherein the provision of the sentence-type rehabilitation content comprises outputting the audio quiz a predetermined number of times based on a plurality of sentences, and wherein the acquisition of the user response data comprises a plurality of pieces of user response data.

5. The method of claim 1, wherein the provision of the sentence-type rehabilitation content comprises providing problem guidance text, an audio quiz start button, and, multiple choice selection items.

6. The method of claim 5, wherein the provision of the sentence-type rehabilitation content further comprises providing wrong answer guidance text, a skip button, and a restart button when the user response data is processed as a wrong answer.

7. The method of claim 1, wherein the correct answer learning model, when a predetermined text is input, outputs:

(i) correct answer pattern information including text structure arrangement information and grapheme combination structure information based on the predetermined text; and (ii) correct answer probability information indicating a probability that the user will correctly answer an audio quiz corresponding to the predetermined text.

8. The method of claim 1, wherein the wrong answer learning model, when a predetermined text is input, outputs:

(i) wrong answer pattern information that models an analyzed type of wrong answer by grapheme, based on text structure arrangement information and grapheme combination structure information of the predetermined text; and (ii) wrong answer probability information indicating a probability that the user will incorrectly answer an audio quiz corresponding to the predetermined text.

9. The method of claim 1, wherein the problem pattern data includes a content identification code, base text, and analysis data.

10. The method of claim 9, wherein the base text is text data that serves as the basis for forming the audio quiz provided based on the sentence-type rehabilitation content.

11. The method of claim 9, wherein the analysis data includes a morpheme analysis corpus list according to the base text and grapheme separation data according to the morpheme analysis corpus, as analyzing the structure of the base text.

12. The method of claim 11, wherein the grapheme separation data includes a plurality of grapheme-separated morphemes and positional information for each of the grapheme-separated consonants or vowels.

* * * * *